US006984394B2

(12) United States Patent
Menz et al.

(10) Patent No.: US 6,984,394 B2
(45) Date of Patent: *Jan. 10, 2006

(54) PLASTICALLY DEFORMABLE IMPLANT

(75) Inventors: Dirk-Henning Menz, Diedorf (DE); Joachim Dresp, Munich (DE)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/832,516

(22) Filed: Apr. 27, 2004

(65) Prior Publication Data

US 2004/0197376 A1    Oct. 7, 2004

Related U.S. Application Data

(63) Continuation of application No. 10/018,372, filed as application No. PCT/EP00/05208 on Jun. 7, 2000.

(30) Foreign Application Priority Data

Jun. 12, 1999   (DE)   ................................. 199 26 889

(51) Int. Cl.
```
A61F 2/02       (2006.01)
A61F 2/14       (2006.01)
A61K 47/30      (2006.01)
```
(52) U.S. Cl. ................ 424/423; 424/78.04; 514/772.3; 523/115; 523/116
(58) Field of Classification Search ................ 424/423, 424/78.04; 514/772.3; 523/115, 116
See application file for complete search history.

(56) References Cited

U.S. PATENT DOCUMENTS

| 4,490,351 A | 12/1984 | Clark, Jr. |
| 5,573,757 A * | 11/1996 | Riess et al. ............... 424/78.02 |
| 6,262,126 B1 | 7/2001 | Meinert |

FOREIGN PATENT DOCUMENTS

WO   WO 97/12852   4/1997

OTHER PUBLICATIONS

MP Krafft et al, Highly fluorinated amphiles and colloidal systems, and their applications in the biomedical field. A contribution, pp 489-514, Biochimie (1998) 80, 489-514.

* cited by examiner

*Primary Examiner*—Carlos A. Azpuru
(74) *Attorney, Agent, or Firm*—Martin Fleit; Paul D. Bianco; Fleit Kain Gibbons Gutman Bongini & Bianco P. L.

(57) ABSTRACT

The invention relates to a plastically deformable implant for inserting into bodily orifices of the human or animal body. Implants of this type are used, for example, in ophthalmology, in particular, as vitreous body or lens replacements and in dentistry, for example, for filling extraction cavities in jaw-bones. Known implants, however, are not suitable for long-term use. The invention aims to provide a deformable plastic implant which also has a long-term application. This is achieved by the fact that the implant consists of a gel which is not sealed, containing fluorocarbon and which is directly introduced into the natural, or artificially created bodily orifice.

16 Claims, 1 Drawing Sheet

PLASTICALLY DEFORMABLE IMPLANT

RELATED APPLICATION

This application is a continuation of application Ser. No. 10/018,372, filed Dec. 12, 2001, which was filed as the National Stage of International Application No. PCT/EP00/05208, filed Jun. 7, 2000, which claims priority under 35 U.S.C. §119 from German application 199 26 889.4, filed Jun. 12, 1999, the content of all of which are incorporated by reference in their entirety. Applicant claims the benefit of 35 U.S.C. §120.

FIELD OF THE INVENTION

The invention relates to a plastically deformable implant.

BACKGROUND OF THE INVENTION

Such plastically deformable implants are used, for example, in ophthalmology, in particular as vitreous body or lens replacement, and in dentistry, for example, for filling cavities left after tooth extraction in the jaw bone.

In addition, in plastic surgery, it is known to use deformable implants which, however, invariably comprise a cushion-like envelope and an implant material as a filler, thus providing a barrier with respect to the surrounding tissue and thereby ensuring biocompatibility.

For ophthalmological applications, fluorine-containing compounds in the form of readily moving liquids and preparations are known. In this field of application, the properties typical for fluorine-containing compounds, such as high density and low surface tension, are utilized. The partially fluorinated and perfluorinated compounds so far used, however, are single-phase liquids. As a result, varying material properties can be utilized only to the extent defined by the structure and the inherent properties of the chemical compounds used. Thus, with the conventionally known fluorine-containing ophthalmological preparations it is not possible to meet the frequently highly different and in part opposite requirements of the preparation with one single material component.

Thus, for example, during and after vitreoretinal interventions, a preparation is needed which has excellent tamponade properties and, at the same time, offers the possibility of an exchange of water-soluble substances, which cannot be simultaneously achieved with the well-known ophthalmological preparations since these do not mix with water. In addition, an attempt was made to avoid injury to the retina—which is observed during the ophthalmological application of perfluorocarbons and which is to be attributed to mechanical effects—by using substances with a lower density, such as those described in European Patent No. 563 446 B1 and German Patent Nos. DE 197 19 280 and DE 195 36 504 A1. Unfortunately, this entailed a simultaneous increase in the lipophilic properties of these compounds, which led to penetration. As a result, histological changes as well as side effects similar to those known from perfluorocarbons were observed.

In addition, in prior art, it has been known to use fluorine-containing gels of the class of fluorocarbon-water emulsions. Emulsions in the form of gels of this type and their possible applications in medicine and technology have been described, for example, in U.S. Pat. No. 5,573,757, in European Patent No. EP 0 340 079, and in International Patent No. WO 97/03644. These gels form polyaphron structures with a continuous minority phase and a discontinuous majority phase. During this process, the minority phase completely encapsulates the majority phase and thus determines the most important properties of the overall preparation. As known from prior art, a very specific working sequence must be followed in order to produce preparations with this type of structure. Furthermore, it is also known from prior art that in gels of this type, a destruction or liquefaction, for example, by means of heat or mechanical pressure, is irreversible, i.e., once a gel has been destroyed, its original gel structure cannot be restored. This has been described in articles published by M. P. Kraff and J. G. Riess in Angew. Chem. 106 (1994), p. 1146, and by H. Hoffmann and G. Ebert in Angew. Chem. 100 (1988), p. 933.

In addition, the fluorine-containing gels known from prior art have an affinity both to water and to body tissues. When such gels are used over long periods of time in aqueous media or in body tissue, this affinity to water and tissue leads to a liquefaction and destruction of the gels. This, together with the fact that the gel, once destroyed, cannot have its structure restored since the destruction is irreversible prevents the long-term use of this gel as an implant in body tissue.

SUMMARY OF THE INVENTION

Thus, the problem to be solved by the present invention is to make available a plastically deformable implant which can be inserted into natural or artificially created bodily orifices of the human or animal body and which at the same time is also suitable for long-term use.

This problem is solved by the characterizing clauses of claim 1. Useful embodiments and applications of the implant according to the present invention can be taken from the dependent claims.

BRIEF DESCRIPTION OF THE DRAWINGS

A mare complete understanding of the present invention, and the attendant advantages and features thereof, Will be inure readily understood by reference to the following detailed description when considered in conjunction with the accompanying drawings wherein.

DETAILED DESCRIPTION OF THE EMBODIMENTS

Figure 1:
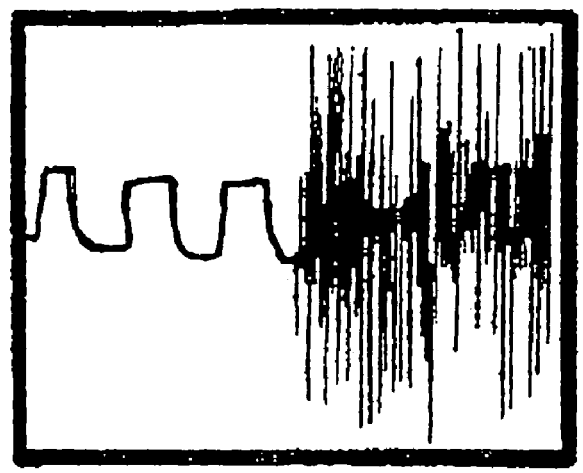
FIG. 1: Measurerecat of pressure peaks during the acceleration of perfluorophenanthrene in a sealed glass tube, end-scale deflection corresponds to 70 mbar (52.5 mm Hg).

Because of their versatile and variable properties, the fluorine-containing gels described above are suitable for use as a starting material in the construction of a generic implant. For such an implant to be of long-term use, however, it must be ensured that the implant does not irreversibly liquefy when exposed to aqueous media. In addition, the implant must have a long-term stability to mechanical and thermal stresses. The stability of the implant material on exposure to heat must be ensured, in particular, because the material must be sterilized (121° C.) prior to inserting it into the bodily orifices. One finding on which the present invention is based relates to the fact that the gel structure of certain fluorine-containing gels is reversible and can be completely recovered even after it has been considerably damaged.

Compared to the prior printed publications on fluorine-containing gels, this finding comes as a surprise.

According to the present invention, the term fluorine-containing gel is defined as a gel-like preparation which comprises a minimum of one fluorocarbon. In especially useful embodiments of the present invention, the fluorine-containing gel comprises essentially three components, i.e., a fluorocarbon, a fluorine-containing surface-active agent, and water. It is possible for different additives to be added to the fluorocarbon-containing and aqueous components. Certain compositions of surface-active agents, fluorocarbons, and water form gels which are able to completely recover their gel structure after they have been liquefied, for example, by exposure to mechanical pressure or heat. This property of the gels according to the present invention makes it possible for them to be used as a generic implant over a long period of time. If the implant material of such an implant that has been inserted into a bodily orifice were to liquefy, for example, as a result of short-term pressure, the gel structure, due to the reversibility described, would be able to recover when in a state of rest. Thus, the implant according to the present invention has a self-regulating restorative mechanism. This self-regulating restorative mechanism of a polyaphron gel is attributable to the stability of the aphrons that form the gel. After liquefaction, a gel can restore its structure only if its "building blocks," the aphrons, were not completely destroyed. If a sufficient number of intact aphrons remain after liquefaction, a recovery is possible, and what comes as a surprise is the fact that the aphron structure is transferred to the homogenized regions of the surrounding liquid and that the gel structure is restored in the entire liquid. The stability of the aphrons depends on the intensity of the interaction between water, surface-active agent, and perfluorocarbon, which in turn is determined by the surface properties and the ability of the individual phases to spread on each other's surface. In addition, an important aspect is the intensity of the interactions of the molecules within the films that envelop the aphrons (water/surface-active agent; perfluorocarbon/surface-active agent). Thus, the self-regulating restorative mechanism is activated only if the surface properties of the surface-active agent/water and/or surface-active agent/perfluorocarbon film, on the one hand, and of the internal aphron phase, on the other hand, are properly coordinated, i.e., if the strength of the surface-active agent stabilizes the aphron structure. This can be implemented through the use of fluorine-containing surface-active agents of the general formula

where $R_F$ stands for the linear or branched perfluoroalkyl groups with more than 5 carbon atoms and $R_{pol}$ stands for a polar hydrocarbon residue which comprises a minimum of one functional group which is selected from CO—NH(R), CO—N(R)$_2$, COO—, COOR, SO$_3$; SO$_2$N(R)$_2$, CH$_2$—O—R, PO$_2$H, PO$_3$H. The molecular weight is preferably >400 g/mol, the surface tension in aqueous solution is <30 mN/m and preferably <20 mN/m. The interfacial tension in aqueous solution with respect to the nonpolar component is <25 mN/m, preferably <10 mN/m, and the concentration is <3%, preferably <0.1%. With nonfluorinated surface-active agents, this can be achieved by means of a strong cohesive effect with an HLB value greater than 25 (HLB=hydrophilic lipophilic balance according to Griffin in J. Soc. Cosmet. Chem. 1 (1949), p. 311).

Thus, the implant according to the present invention is able to resist both thermal stress, for example, during sterilization, and mechanical stress, for example, pressure exerted on the bodily orifice. Furthermore, the ability of the implant according to the present invention to reverse the damage to its structure prevents the destruction of the implant material that is caused by diffusion processes in the bodily orifices. In the implants according to the present invention, the light transmittance of the fluorine-containing gels which in other gels is generally considerably impaired as a result of these diffusion processes remains in a dynamic equilibrium.

The biocompatibility of the implants according to the present invention is ensured since ultrapurified starting materials and very small quantities of surface-active agents (preferably <0.1%) are used. Moreover, the surface-active agents used are histocompatible, intimately bonded to the gel, and homogeneously distributed throughout the entire volume.

The implant according to the present invention is used, for example, in ophthalmology as a vitreous body replacement. For this purpose, in particular fluorine-containing gels with a high specific weight and, at the same time, a high affinity to water-soluble substances are suitable. Thus, for the first time, a tamponading material or implant with a specific weight higher than that of water and, at the same time, the capacity to absorb water-soluble ions are made available. After vitrectomy and conventional procedures of retinal surgery, the plastically deformable implant is injected into the space of the vitreous body. As a result of the absorption of water, the plastically deformable implant expands. The increase in volume caused by the absorption of water enhances the tamponade effect mediated by the highly dense fluorocarbons. At the same time, pressure builds inside the implant, and this pressure counteracts a further expansion in volume and absorption of water. The dynamic equilibrium that is established as a result is ensured by the structural reversibility of the implant material and thus makes it possible for the implant to be used for long-term applications.

An additional advantage of the implant according to the present invention when used as a vitreous body replacement is the reduction of mechanical injuries in the region of the retina. Such injuries are known to arise when pure fluorocarbons are used as vitreous body replacement materials and have been attributed to the high density of the fluorocarbons. Only recently it was discovered that the injury is not caused by the static pressure. Instead, the injuries are attributable to the fact that the impalement of heavy fluids on the retina—as it occurs, for example, when the head is moved rapidly—causes an increase in the mechanical pressure. When using fluorine-containing gels as vitreous body replacement materials, this effect can be prevented through the use of certain gels. These gels are gels with a high viscosity/density ratio of >100 mPa cm$^3$/g, preferably >1000 mPa cm$^3$g. Gels according to the present invention of this type make possible a tamponade in the lower eye segment without the development of motion-induced pressure peaks during sudden jerky head movements. This is made possible by the viscosity which—in comparison to that of pure fluorocarbons—is increased, and this increased viscosity counteracts the acceleration forces and prevents the damaging impact of heavy fluids on the retina. In this context, it is a particular advantage that compared to the material properties of pure fluorocarbons, those of the fluorine-containing gels are variable within wide limits.

In contrast to all other ophthalmological preparations on the basis of fluorinated compounds, the implants according to the present invention as ophthalmological preparations for application in the vitreoretinal region can be used not only in procedures that aim at the reattachment of the retina and as a short-term tamponading material. Instead, in addition to the tamponade effect, these implants can also perform other functions of the natural vitreous body. Thus, these implants open up new possibilities, such as treating pathological changes in the vitreoretinal region or suppressing morbid processes which may lead to a permanent injury to the retina, e.g., injury to the Müller cells. For this purpose, the preparations can be designed to ensure that they combine different and even opposite properties in such a way that these can be activated in one single treatment step. The application potential of the gels is enhanced and expanded by the fluorocarbons that are contained in the gels which, as is well known, have special properties, such as anti-inflammatory and anti-gas properties.

The other known properties of fluorine-containing compounds that are of advantage when such compounds are applied as ophthalmological preparations are maintained or even enhanced in the implants according to the present invention, thus, for example, the possibility of a laser treatment, the tamponade properties, and the solubility of active ingredients. The implants according to the present invention can be removed from the bodily orifices using conventional methods, for example, vitrectomy.

The fluorine-containing implants according to the present invention can also be used as intraocular lenses. For this particular purpose, it is recommended that highly transparent gels be used which have an especially high viscosity/density ratio; this can be achieved in particular through the use of oligomer $R_F F_H$ compounds as the discontinuous phase, such as has been described in the European Patent No. EP-A 545 174. In addition, the refractive index of the gels used should be adjusted to a range from 1.334 to 1.338, which can be implemented, for example, by using the following compounds:

| Fluorocarbon | Surface-active agent Name/structure/abbreviation/ characteristics | Refractive index | Biocompatibility (Draize test) |
|---|---|---|---|
| Perfluorophenanthrene | Perfluoroalkyl ethanol oxethylate (Fluowet OTN, Clariant) $\sigma_O = 18$ mNm, $\sigma_G = 19$ mNm | 1.3357 | n.d. |
| Perfluorophenanthrene | Fluorinated amine oxide (Fluowet OX, Clariant) $\sigma_O = 22$ mNm, $\sigma_G = 12$ mNm | 1.3361 | n.d. |
| Perfluorophenanthrene | Perfluoroalkyl ethanol oxethylate (Fluowet OTL, Clariant) $\sigma_O = 19$ mNm, $\sigma_G = 10$ mNm | 1.3355 | neg. |
| Perfluorophenanthrene | Perfluorooctanoic acid tetraethyl piperazinium salt (HO224) $\sigma_O = 16$ mNm | 1.3362 | neg. |
| Perfluorophenanthrene | Perfluorooctanoic acid N-methyl-D-glucamide (T14) $\sigma_O < 20$ mNm | 1.3360 | neg. |
| Perfluorophenanthrene | Perfluorooctanoic acid diethanolamide (HO31) $\sigma_O < 20$ mNm | 1.3358 | neg. |
| Perfluorophenanthrene | Tetramethyl ammonium salt of perfluorooctanoic acid (E 749) $\sigma_O < 20$ mNm | 1.336 | neg. |
| Perfluorophenanthrene | Perfluorooctanoic acid amidotrimethyl ammonium iodide (B98) $\sigma_O < 20$ mNm | 1.336 | neg. |
| Perfluorophenanthrene | Tetraethyl anmonium salt of perfluorooctanesulfonic acid (B248) $\sigma_O < 20$ mNm | 1.3359 | neg. |
| Perfluorophenanthrene | Perfluorodecanoic acid N-(2-hydroxyethyl)-D-glucamide (T21) $\sigma_O < 20$ mNm | 1.3357 | neg. |
| Perfluorophenanthrene | Perfluorooctanoic acid N-(2-hydroxyethyl)-D-glucamide (T16) $\sigma_O < 20$ mNm | 1.336 | neg. |
| $C_6P_{13}C_8H_{17}$ | Tetramethyl ammonium salt of perfluorooctanoic acid (E749) $\sigma_O < 20$ mNm | 1.3463 | n.d. |
| $(C_6F_{13}C_2H_4)_3$ | Tetramethyl ammomium salt of perfluorooctanoic acid (E 749) $\sigma_O < 20$ mNm | 1.3357 | n.d. | neg. = negative
n.d. = not determined
$\sigma_O$ = surface tension
$\sigma_G$ = interfacial tension with respect to the nonpolar component The implants according to the present invention can be used instead of the artificial intraocular lenses made of silicone, PMMA, or acrylic that are normally used for cataract operations. After opening the capsular sac and removing the cloudy natural lens using conventionally known methods, the implant material is injected, ensuring that the entire capsular sac is completely filled with it. The implant takes over the complete function of the natural lens, i.e., in spite of the cataract operation, the accommodative capacity of the lens is maintained. Due to the forces that are continuously acting on the implant, the mechanical long-term stability is of very special importance in this particular application.

The implants according to the present invention can also be used to temporarily seal off bodily orifices and to temporarily separate tissue parts, for example, in applications in which the implants are used as expanders, or to stimulate the growth of bone. In dentistry, the implant according to the present invention can be used in particular to temporarily fill extraction cavities in the jaw bone and to expand tissue. In addition, it can be used in orthopedic medicine as a biocompatible lubricating film for joints and joint prostheses. After inserting the implant material into the extraction cavities, these cavities are encapsulated by sewing together the surrounding tissue. This prevents leakage of the gel-like implant.

The practical examples described below will explain the choice of the implant materials and their preparation in greater detail. In the explanation, reference is made to the accompanying drawings. As can be seen, these drawings include:

FIG. 1: Measurement of pressure peaks during the acceleration of perfluorophenanthrene in a sealed glass tube, end-scale deflection corresponds to 70 mbar (52.5 mm Hg).

Figure 2:
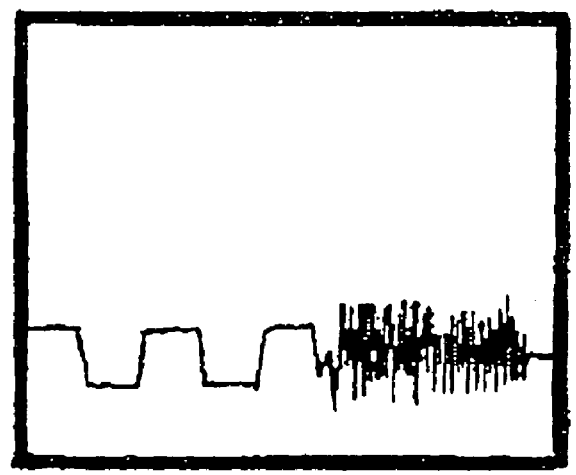
FIG. 2: Measurement of pressure peaks during the acceleration of an implant material according to the present invention in a sealed glass tube, end-scale deflection corresponds to 70 mbar (52.5 mm Hg).

FIG. 2: Measurement of pressure peaks during the acceleration of an implant material according to the present invention in a sealed glass tube, end-scale deflection corresponds to 70 mbar (52.5 mm Hg).

EXAMPLE 1

Using ultrasound, a mixture of 99% fluorocarbon, 0.9% isotonic physiological saline solution, and 0.1% OTL is prepared from perfluorophenanthrene which has been ultra-purified according to a well-known method (European Patent No. EP 0 626 936 B1), isotonic physiological saline solution and Fluowet OTL (firm of Clariant); a polyaphron gel in a volume concentration of less than 30% which has been prepared according to conventional methods is slowly added to this solution until the entire mixture solidifies to form a gel. The preparation turns completely transparent after the gas is carefully removed from it or it is centrifuged.

By subjecting this implant material to alternating mechanical stresses, such as heating to approximately 130° and/or adding water, it is possible to completely liquefy the material. By adding light mechanical energy or cooling or removing water through an absorbent material (dry glass filter, etc.), the gel is returned to its original state. This procedure can be repeated several times, without changing the composition of the plastically deformable implant material.

EXAMPLE 2

A plastically deformable implant material which has been prepared according to the instructions described in Example 1 is covered with twice the quantity of water. As a result, the gel-like phase expands. When the volume is limited, e.g., by a semipermeable bottom, an increased pressure begins to build up inside the material until the water on which pressure is exerted from one side exits and flows off on the other side, without destroying the gel structure.

EXAMPLE 3

An implant material which has been prepared according to the instructions described in Example 1 and which contains T14 instead of OTL (firm of Clariant), is covered with three times the quantity of water. Instead of the original phase boundary, a thin third phase forms. By especially adjusting the diffusion rates from the boundary layer of the implant and the depth of the volume of gel, it is possible to obtain a perfluorophenanthrene barrier layer which prevents a further dilution of the gel or the breakdown of the gel. This ensures that a stability over a very long time is achieved.

EXAMPLE 4

A gel which has been prepared according to the instructions described in Example 1 is placed into a glass tube which can be sealed on both ends. A sensitive pressure sensor is coupled to one end of the glass tube. Subsequently, the glass tube is shaken and positioned so as to ensure that alternately one of the opening points downward. The same test is repeated, except that water and perfluorophenanthrene instead of the plastically deformable implant are used (FIG. 1). As a result of the viscosity/density ratio of >3000 mPa cm$^3$/g, a tamponade effect appropriate to the perfluorocarbons can be achieved by the implant material, without entailing the pressure peaks observed as a result of centrifugal or shaking motions (given an incomplete filling up to 50 mm of mercury), such as are observed with pure perfluorocarbons. In ophthalmological applications, the pressure peaks must not exceed the tolerable intraocular pressure (20, for a short time, 30 mm of mercury). Thus, the plastically deformable implant has a characteristics profile that is highly suitable for use in ophthalmological applications, which profile is a prerequisite for the long-term use as a vitreous body replacement material and, at the same time, it is able to prevent mechanical injury to the retina (FIG. 2).

EXAMPLE 5

According to the method described in Example 1, it is possible to use, e.g., sodium dodecyl sulfate (SDS) HBL 40 or Pluoronic F68 (F68) HLB 29, as surface-active agents in the production of the implants according to the present invention. In both cases the fluorocarbon used is perfluorophenanthrene. The substances can be sterilized at 121° C.

The invention claimed is:

1. A plastically deformable implant for insertion into bodily orifices of a human or animal body, the implant formed by a gel which is not sealed and is directly introduced into a natural or artificially created bodily opening, with the gel having a polyaphron structure and comprising a fluorocarbon selected from the group consisting of perfluorophenanthrene, $C_6F_{13}C_8H_{17}$ and $(C_6F_{13}C_2H_4)_3$, further comprising water, and a minimum of one fluorinated surface-active agent of the general formula $R_F$-$F_{pol}$, wherein:

$R_F$ stands for linear or branched perfluoroalkyl groups with more than 5 carbon atoms;

$R_{pol}$ stands for a polar hydrocarbon residue with a minimum of one functional group which is selected from the group consisting of CO—NH(R), CO—N(R)$_2$, COO—, COOR, SO$_3$—, SO$_2$N(R)$_2$, CH$_2$—O—R, PO$_2$H, and PO$_3$H (R=alkyl); and the surface-active agent has a molecular weight of >400 g/mol, a surface tension in aqueous solution of <30 mN/m, an interfacial tension in aqueous solution with respect to the fluorocarbon of <25 mN/m, and a concentration of <0.3%.

2. The implant of claim 1 wherein the fluorinated surface-active agent is selected from the group consisting of perfluoroalkyl ethanol oxethylate, perfluorooctanoic acid tetraethyl piperazinium salt, perfluorooctanoic acid N-methyl-D-glucamide, perfluorooctanoic acid diethanolamide, tetramethyl ammonium salt of perfluorooctanoic acid, perfluorooctanoic acid amidotrimethyl ammonium iodide, perfluorodecanoic acid N-(2-hydroxyethyl)-D-glucamide and perfluorooctanoic acid N-(2-hydroxyethyl)-D-glucamide.

3. The implant of claim 1 wherein the gel has a viscosity to density ratio greater than 0.1 Pa cm$^3$/g and lower than 3 Pa cm$^3$/g.

4. The implant of claim 3 wherein the ratio is lower than 1 Pa cm$^3$/g.

5. The implant of claim 1 wherein after liquefaction the gel structure is reversible and can be completely restored.

6. The implant of claim 1 wherein the implant is an ophthalmologic implant.

7. The implant of claim 6 wherein the implant is a vitreous body or lens replacement.

8. The implant of claim 7 wherein the implant is permeable by water-soluble and ionic compounds and has a refractive index in a range from 1.334 to 1.338 and has a specific weight greater than 1.05 g/cm$^3$.

9. The implant of claim 1 wherein the implant is a dental implant.

10. The implant of claim 9 wherein the implant is configured and dimensioned for filling extraction cavities in the jaw bone.

11. The implant of claim 1 wherein the implant is a tissue expander.

12. A method of treating tissue comprising the steps of inserting an implant formed in accordance with claim 1 into a bodily orifice located proximal to tissue to be treated, and treating the tissue to be treated with an oxygen therapy.

13. A method for treating a human or animal body comprising forming an implant as defined in claim 1, and implanting said implant into a bodily orifice of a human or animal.

14. A method for treating a human or animal eye in a cataract operation comprising opening the capsular sac and removing the cloudy natural lens, injecting an implant as defined in claim 1, ensuring that the entire capsular sac is completely filled with it; wherein the implant takes over the complete function of the natural lens.

15. A method of manufacture of an implant as defined in claim 1, comprising preparing a mixture of 99% of the ultra-purified fluorocarbon, 0.9% isotonic physiological saline solution and 0.1% of the fluorinated surfactant with the use of ultrasound, adding a conventionally prepared polyaphron gel in a volume concentration of less than 30% slowly to the said mixture, until the entire mixture solidifies to form a gel.

16. The method of claim 15, wherein the so-formed gel is either degassed or centrifuged.

* * * * *